(12) United States Patent
Bord

(10) Patent No.: US 10,258,705 B2
(45) Date of Patent: Apr. 16, 2019

(54) SANITIZING DEVICE FOR TOOL AND CART HANDLES

(71) Applicant: Patrick Daniel Bord, North Miami, FL (US)

(72) Inventor: Patrick Daniel Bord, North Miami, FL (US)

(*) Notice: Subject to any disclaimer, the term of this patent is extended or adjusted under 35 U.S.C. 154(b) by 432 days.

(21) Appl. No.: 14/874,424

(22) Filed: Oct. 3, 2015

(65) Prior Publication Data

US 2016/0095948 A1 Apr. 7, 2016

Related U.S. Application Data

(60) Provisional application No. 62/125,550, filed on Jan. 26, 2015, provisional application No. 62/071,786, filed on Oct. 3, 2014.

(51) Int. Cl.
*A61L 2/22* (2006.01)
*A61L 2/18* (2006.01)

(52) U.S. Cl.
CPC .. *A61L 2/22* (2013.01); *A61L 2/18* (2013.01)

(58) Field of Classification Search
CPC .................................... A61L 2/18; A61L 2/22
See application file for complete search history.

(56) References Cited

U.S. PATENT DOCUMENTS

| | | |
|---|---|---|
| 2,147,769 A | 2/1939 | Epstein |
| 3,224,029 A | 12/1965 | Domingos |
| 3,866,649 A | 2/1975 | Bringmann |
| 4,554,696 A | 11/1985 | Nye, Jr. |
| 4,923,316 A | 5/1990 | Fattal |
| 4,953,999 A | 9/1990 | Rivers |
| 5,269,615 A | 12/1993 | Lewis, Jr. |
| 5,492,425 A | 2/1996 | Carter et al. |
| 5,715,571 A | 2/1998 | Fasano |
| 5,820,142 A | 10/1998 | Duer |
| 6,065,764 A | 5/2000 | Moseley |
| 6,645,435 B2 | 11/2003 | Dawson et al. |
| 6,981,707 B1 | 1/2006 | Dandy |
| 7,222,817 B2 | 5/2007 | Stringer |
| D573,321 S | 7/2008 | Dean |
| 7,611,156 B2 | 11/2009 | Dunser |
| 7,878,371 B2 | 2/2011 | Sassoon |
| 2004/0021279 A1 | 2/2004 | Sobo et al. |
| 2005/0267233 A1 | 12/2005 | Joshi |

(Continued)

*Primary Examiner* — Sean E Conley
(74) *Attorney, Agent, or Firm* — Patent CEO, LLC; Phillip Vales

(57) ABSTRACT

The sanitizing device for tool and cart handles is designed to rest on a base mount attached to the tool handle. When the user wants to use the sanitizing device they move the device from its rest position, spray sanitizing solution onto the desired surface area of the tool or cart handle, then slide the device along the handle to sanitize and/or disinfect it. The device includes a sponge which aids in the thorough sanitization of the desired surface area. In addition to sanitizing tool or cart handle, the device allows the user to direct the sanitizing spray into their hands to eliminate or minimize the transfer or spread of communicable pathogens. The fluid reservoir may be refillable or, alternatively, the fluid reservoir may be disposable and replaceable when the fluid is depleted.

12 Claims, 2 Drawing Sheets

(56) References Cited

U.S. PATENT DOCUMENTS

| | | | |
|---|---|---|---|
| 2006/0076743 A1* | 4/2006 | Dunser | B08B 9/023 |
| | | | 280/33.992 |
| 2009/0199360 A1 | 8/2009 | Madanat | |
| 2011/0226801 A1* | 9/2011 | Smith-Heskel | A61L 2/18 |
| | | | 222/1 |
| 2012/0181405 A1* | 7/2012 | Zlatic | A47G 23/0225 |
| | | | 248/313 |
| 2015/0097005 A1* | 4/2015 | Mireles | A61L 2/16 |
| | | | 222/173 |

* cited by examiner

SANITIZING DEVICE FOR TOOL AND CART HANDLES

CROSS REFERENCE TO RELATED APPLICATIONS

This application claims priority to U.S. Provisional Patent Application No. 62/071,786, filed Oct. 3, 2014 and entitled "Sanitizing Handle Brush," and U.S. Provisional Patent Application No. 62/125,550, filed Jan. 26, 2015 and entitled "Sani Slide." The prior applications are fully incorporated herein by reference and priority is claimed with respect thereto to the extent permitted by law.

FIELD OF THE INVENTION

This invention is related to sanitizing implements. More particularly, this invention relates to devices utilized to sanitizing cleaning tools.

BACKGROUND

Hand-operated tools and carts often have many different users. The handles of such hand-operated devices may contain high levels of bacteria, germs and viruses. Exposure to such pathogens poses a potential health hazard to users. While sanitary gloves, anti-bacterial wipes and prophylactic barriers may provide some protection to pathogenic exposure for an individual user, they are expensive and inconvenient for multiple different users.

Thus, there is a need in the art for a cost effective, functional and easy-to-use portable system to sanitize and/or disinfect the handles of hand-operated tools and carts as well as the hands of the user.

SUMMARY

In certain example embodiments described herein, a portable device provides for efficiently and economically sanitizing and/or disinfecting the handles of hand-operated tools and carts as well as the hands of the user.

A sanitizer comprising:
a fluid reservoir mounted in
a snap-in holder having an integral top and an integral bottom; wherein the top of the snap-in holder further comprises a first protruding end and a second protruding end; such that the first protruding end further comprises:
a forward set of reservoir locking arms integrally associated with the top of the snap-in holder such that the forward set of reservoir locking arms comprises: a first arm and a second arm; and such that the second protruding end further comprises:
a rear locking protrusion connected to a first side and to another side of the snap-in holder; wherein the rear locking protrusion is integrally associated with the top of the snap-in holder; and
wherein the forward set of reservoir locking arms is disposed at a first end of the snap-in holder and wherein the rear locking protrusion is disposed at another end of the snap-in holder;
a sponge mount region on the integral bottom of the snap-in holder
a sponge attached to the sponge mount region on the integral bottom of the snap-in holder.
In another aspect, whereby said sanitizer further comprises the rear locking protrusion having a reservoir receiving opening therein.

In another aspect, wherein the integral bottom further comprises:
a an integral receiving mouth characterized in that the integral receiving mouth is not attached to a surface to be cleaned during periods of non use of the sanitizer.
In another aspect, wherein the integral bottom of the snap-in holder further comprises:
a mouth.
In another aspect, wherein the integral bottom of the snap-in holder is partially circular.
In another aspect, wherein the fluid reservoir further comprises:
a forward recessed portion associated with the forward set of reservoir locking arms.
In another aspect, wherein the fluid reservoir further comprises:
a rear recessed portion associated with the rear locking protrusion having the reservoir receiving opening therein.
In another aspect, wherein the fluid reservoir further comprises:
a forward dispensing cap attachment portion.
In another aspect, wherein the fluid reservoir further comprises:
a forward recessed portion associated with the forward set of reservoir locking arms; and
a rear recessed portion associated with the rear locking protrusion having the reservoir receiving opening therein.
In another aspect, wherein the fluid reservoir further comprises:
a forward recessed portion associated with the forward set of reservoir locking arms; and
a forward dispensing cap attachment portion.
In another aspect, wherein the fluid reservoir further comprises:
a forward recessed portion associated with the forward set of reservoir locking arms;
a rear recessed portion associated with the rear locking protrusion having the reservoir receiving opening therein; and
a forward dispensing cap attachment portion.
A disinfecting system comprising:
a mount separably attached to
a reservoir having
a forward region of the reservoir removably attached to
a forward set of reservoir locking arms integrally associated with a top of the mount, such that the forward set of reservoir locking arms comprises: a first arm and a second arm integrally associated with the mount at a first end thereof;
a rear locking protrusion integrally associated with the mount at a first side and at another side of the mount; wherein the rear locking protrusion has a reservoir receiver therein, and such that the the rear locking protrusion is disposed at another end of the mount and at the top of the mount; and
a bottom of the mount has an integral tool receiving mouth characterized in that the integral tool receiving mouth is not attached to a surface to be cleaned during periods of non use of the disinfecting system;
a sponge mount region on the bottom of the mount; and
a sponge attached to the sponge mount region on the integral bottom of the mount.
These and other aspects, objects, features, and advantages of the example embodiments will become apparent to those having ordinary skill in the art upon consideration of the following detailed description of illustrated example embodiments.

DETAILED DESCRIPTION OF THE EMBODIMENTS

The device described herein enables the user to efficiently sanitize and/or disinfect the handle of a hand-operated tool such as a mop or broom, or the handle of a hand-operated cart such as a dolly or shopping cart. The device further enables the user to control the flow of the sanitizing and/or disinfecting solution, thereby allowing the user to conveniently sanitize their own hands so as not to transfer or spread of any communicable pathogens. The device is portable and can be easily moved from one tool or cart handle to another, thereby enhancing its cost effectiveness.

The functionality of the various example embodiments will be explained in the following descriptions, read in conjunction with the figures illustrating the devices in detail.

EXAMPLE EMBODIMENTS

Figure 1:
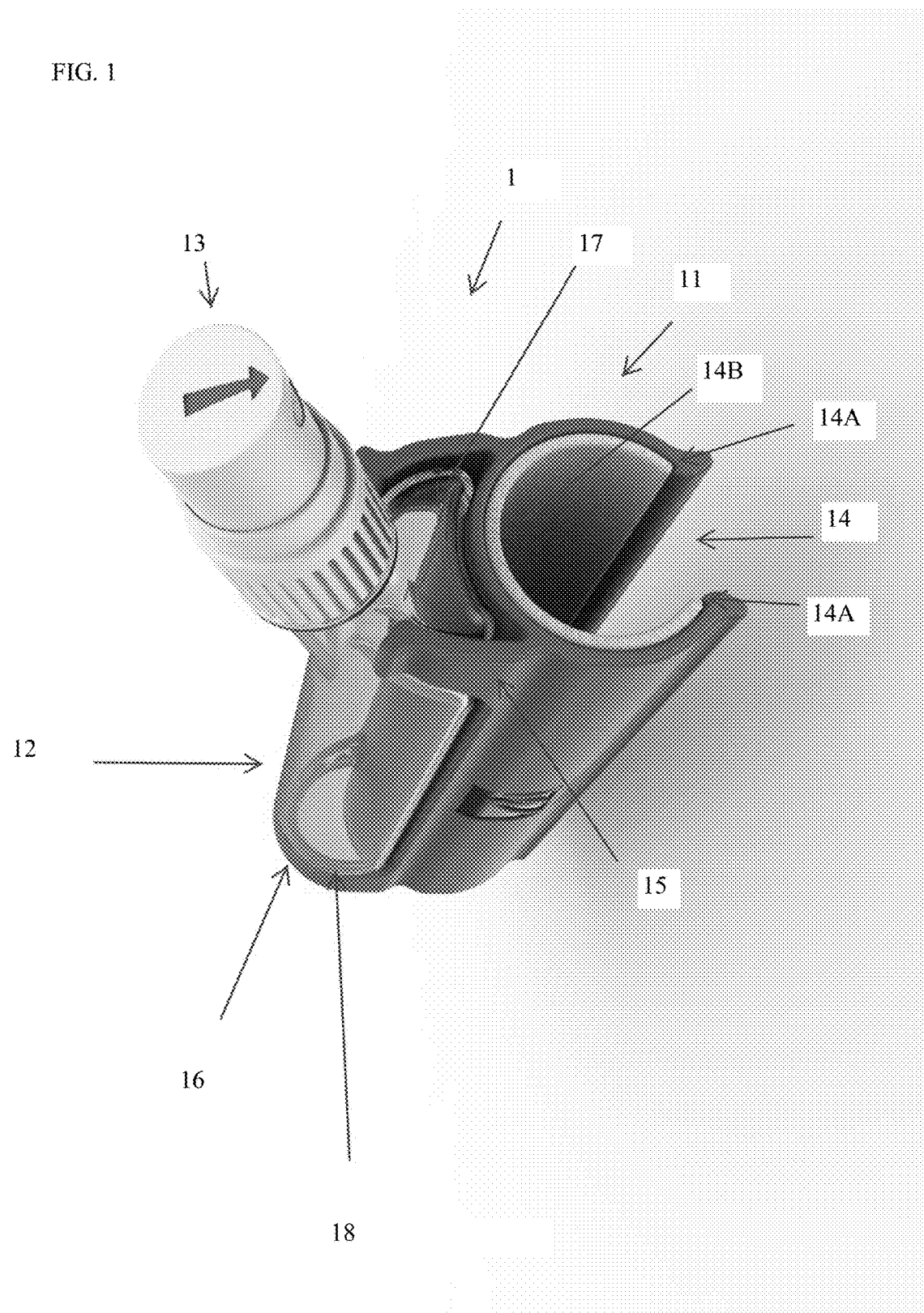
FIG. 1 is an isometric top-front view depicting one embodiment of the handle sanitizing device of the invention presented herein.

FIG. 1 is an isometric top-front view depicting one embodiment of the sanitizing device of the invention presented herein. In this example embodiment, the sanitizing device most generally comprises a plastic snap-in holder 11 which securely locks clear plastic fluid reservoir 12 in place. The device may be clamped around the handle of a tool or cart handle with nominal diameter between ⅞ inches and 1¼ inches or similar such dimensions. A bottom portion of snap-in holder 11 is partially circular having a mouth 14 that permits the insertion of tools and handles for cleansing. Small inwardly projecting edge(s) 14A runs longitudinally down the inner surface of the mouth 14 of the of the snap in holder 11 near the furthest extreme bottom portion of the mouth 14. A disposable/replaceable internal sponge 14B is attached to the inner curved surface of the snap in holder 11 bottom portion via an adhesive affixed to the back thereof. The internal sponge 14B abuts the small inwardly projecting edge(s) 14A forming convenient borders for easy placement within the mouth 14 of the holder 11. The two ends of the bottom portion of snap in holder 11 extend outwards at their respective ends.

The top portion of the snap in holder 11 is formed by a corresponding curved oblong top side that is integral with the bottom portion and has two protruding ends; a first end has two raised snap in arms 15 curving away from then into and upwards and then abruptly extending outwards at their respective ends; a recessed portion 17 of reservoir 12 fits within the two arms 15. A second end of the snap in holder 11 has an opening bounded by a curved integrally formed shape 16 extending from a side of the top portion of the snap in holder 11 to another side thereof; a recessed portion 18 of reservoir 12 fits within the opening bounded by a curved integrally formed shape 16.

It should be understood that a large main body of the reservoir 12 has a concave bottom shape that is designed to sit atop the top main convex portion (curved oblong top side) of the snap in holder 11; also the reservoir has recessed end portions 17, 18 so that these slide within the two arms 15 or within the curved shape 16 respectively. It should also be evident that the reservoir 12 is a generally oblong curved container having one top curved wall and a curved bottom wall that integrates along two respective edges as well two similar smaller recessed portions 17, 18 that integrate therewith along appropriate edges to the top and bottom curved walls and with the spout at recessed portion 17; two end walls integrates with the recessed portions 17, 18.

A forward portion of the reservoir 12 has a circular angled spout having an external thread for attachment of a spray cap 13 having a corresponding internal thread for the mounting thereto; this spout extends out from a top of the recessed portion 17. When the user wants to sanitize and/or disinfect tool or cart handle, they lift the device from its rest position, press spray cap 13 to release sanitizing and/or disinfecting solution onto the desired surface area of the tool or cart handle, and slide the mouth of the snap-in holder 11 across the desired surface area they have chosen to sanitize and/or disinfect. On the inner bottom part of snap-in holder 11 is internal sponge 14 which aids in the thorough sanitization and/or disinfection of the desired surface area. After the user has sanitized the handle, they may twist spray cap 13 in their direction to properly spray the solution into their hands, thus sanitizing their hands and preventing the chance for transfer or spread of any communicable pathogens.

When the user has completed sanitizing and/or disinfecting the tool or cart handle and their hands, the device may be slid to a position where it rests until its next use. Fluid reservoir 12 may be refillable when the fluid is depleted. Alternatively, fluid reservoir 12 may be disposable and replaceable when the fluid is depleted.

Figure 2:
FIG. 2 is an isometric side view depicting the reservoir of the handle sanitizing device.

FIG. 2 is an isometric side view depicting the fluid reservoir of the handle sanitizing device of example embodiment in FIG. 1 as the reservoir 12 is being removed from the snap in holder 11. A forward recessed end 17 and a rear recessed end 18 are narrower then the main body of the reservoir. Thus, as the length of the reservoir body approaches a forward or rear transition point the sides thereof abruptly reduce in size and are shaped appropriately so as to enable them to fit between the arms 15 and the curved bound opening 16. The bottom of the reservoir 12 is concave and follows a curved convex shape of the top portion of the snap in holder 11.

The fluid reservoir includes spray cap 13 which may be rotatable to allow the user to spray sanitizing and/or disinfecting fluid on the tool or cart handle as well as their hands. The fluid reservoir contains solution holding area 22 which may be refillable when the fluid is depleted. Alternatively, the fluid reservoir may be disposable and replaceable when the fluid is depleted. The fluid reservoir may also contain internal sponge 23 which, used in conjunction with internal sponge 14 on snap-in holder 11, aids in the thorough sanitization and/or disinfection of the desired surface area of the tool or cart handle.

What is claimed is:
1. A sanitizer comprising:
   a fluid reservoir mounted in
   a snap-in holder having an integral top and an integral bottom; wherein the top of the snap-in holder further comprises a first protruding end and a second protruding end; such that the first protruding end further comprises:
      a forward set of reservoir locking arms integrally associated with the top of the snap-in holder such that the forward set of reservoir locking arms comprises: a first arm and a second arm;

and such that the second protruding end further comprises:

a rear locking protrusion connected to a first side and to another side of the snap-in holder; wherein the rear locking protrusion is integrally associated with the top of the snap-in holder; and wherein the forward set of reservoir locking arms is disposed at a first end of the snap-in holder and wherein the rear locking protrusion is disposed at another end of the snap-in holder;

a sponge mount region on the integral bottom of the snap-in holder; and a sponge attached to the sponge mount region on the integral bottom of the snap-in holder.

2. The sanitizer of claim 1, whereby said sanitizer further comprises the rear locking protrusion having a reservoir receiving opening therein.

3. The sanitizer of claim 1, wherein the integral bottom further comprises:

an integral receiving mouth characterized in that the integral receiving mouth is not attached to a surface to be cleaned during periods of non use of the sanitizer.

4. The sanitizer of claim 1, wherein the integral bottom of the snap-in holder further comprises:

a mouth.

5. The sanitizer of claim 4, wherein the integral bottom of the snap-in holder is partially circular.

6. The sanitizer of claim 1, wherein the fluid reservoir further comprises:

a forward recessed portion associated with the forward set of reservoir locking arms.

7. The sanitizer of claim 1, wherein the fluid reservoir further comprises:

a rear recessed portion associated with the rear locking protrusion having the reservoir receiving opening therein.

8. The sanitizer of claim 1, wherein the fluid reservoir further comprises:

a forward dispensing cap attachment portion.

9. The sanitizer of claim 1, wherein the fluid reservoir further comprises:

a forward recessed portion associated with the forward set of reservoir locking arms; and a rear recessed portion associated with the rear locking protrusion having the reservoir receiving opening therein.

10. The sanitizer of claim 1, wherein the fluid reservoir further comprises:

a forward recessed portion associated with the forward set of reservoir locking arms; and a forward dispensing cap attachment portion.

11. The sanitizer of claim 1, wherein the fluid reservoir further comprises:

a forward recessed portion associated with the forward set of reservoir locking arms;

a rear recessed portion associated with the rear locking protrusion having the reservoir receiving opening therein; and a forward dispensing cap attachment portion.

12. A disinfecting system comprising:

a mount separably attached to a reservoir having a forward region of the reservoir removably attached to a forward set of reservoir locking arms integrally associated with a top of the mount, such that the forward set of reservoir locking arms comprises: a first arm and a second arm integrally associated with the mount at a first end thereof;

a rear locking protrusion integrally associated with the mount at a first side and at another side of the mount; wherein the rear locking protrusion has a reservoir receiver therein, and such that the the rear locking protrusion is disposed at another end of the mount and at the top of the mount; and a bottom of the mount has an integral tool receiving mouth characterized in that the integral tool receiving mouth is not attached to a surface to be cleaned during periods of non use of the disinfecting system;

a sponge mount region on the bottom of the mount;

a sponge attached to the sponge mount region on the bottom of the mount.

* * * * *